United States Patent [19]

Noble

[11] Patent Number: 4,943,047

[45] Date of Patent: Jul. 24, 1990

[54] HANDGRIP, WITH LIGHT AND TIMER

[76] Inventor: Edward E. Noble, P.O. Box 17238, Jacksonville, Fla. 32245-7238

[21] Appl. No.: 833,115

[22] Filed: Feb. 26, 1986

[51] Int. Cl.⁵ .................. A63B 23/16; A63B 21/00
[52] U.S. Cl. ............................... 272/68; 272/67; 272/DIG. 5; 73/379
[58] Field of Search ...................... 272/68, DIG. 5

[56] References Cited

U.S. PATENT DOCUMENTS

| | | | |
|---|---|---|---|
| 4,216,956 | 8/1980 | Yamamura | 272/DIG. 5 |
| 4,262,898 | 4/1981 | Lee | 272/68 |
| 4,433,364 | 2/1984 | Noble | 272/68 |
| 4,443,008 | 4/1984 | Shimano | 272/DIG. 5 |
| 4,605,221 | 8/1986 | D'Agosta | 272/DIG. 5 |
| 4,613,130 | 9/1986 | Watson | 272/135 |

*Primary Examiner*—Richard J. Apley
*Assistant Examiner*—Joe H. Cheng
*Attorney, Agent, or Firm*—Paul H. Gallagher

[57] ABSTRACT

A pair of handles mounted individually on the ends of a coil spring, the ends of the coil spring extending longitudinally into the ends of the handles, and the coil spring thereby being positioned beyond the handles. A battery is positioned on one handle, and a light bulb and timer in the other handle. A circuit includes conductors, one of which is the coil spring, connecting the battery and the light bulb and timer, and contacts in the ends of the handles that are remote from the coil spring, and upon interengagement of the contacts they complete the circuit and turn on the light bulb and the timer. In squeezing the handles, in exercising the hand, illumination of the light signals the interengagement of the handles. The light bulb also illuminates the timer.

1 Claim, 1 Drawing Sheet

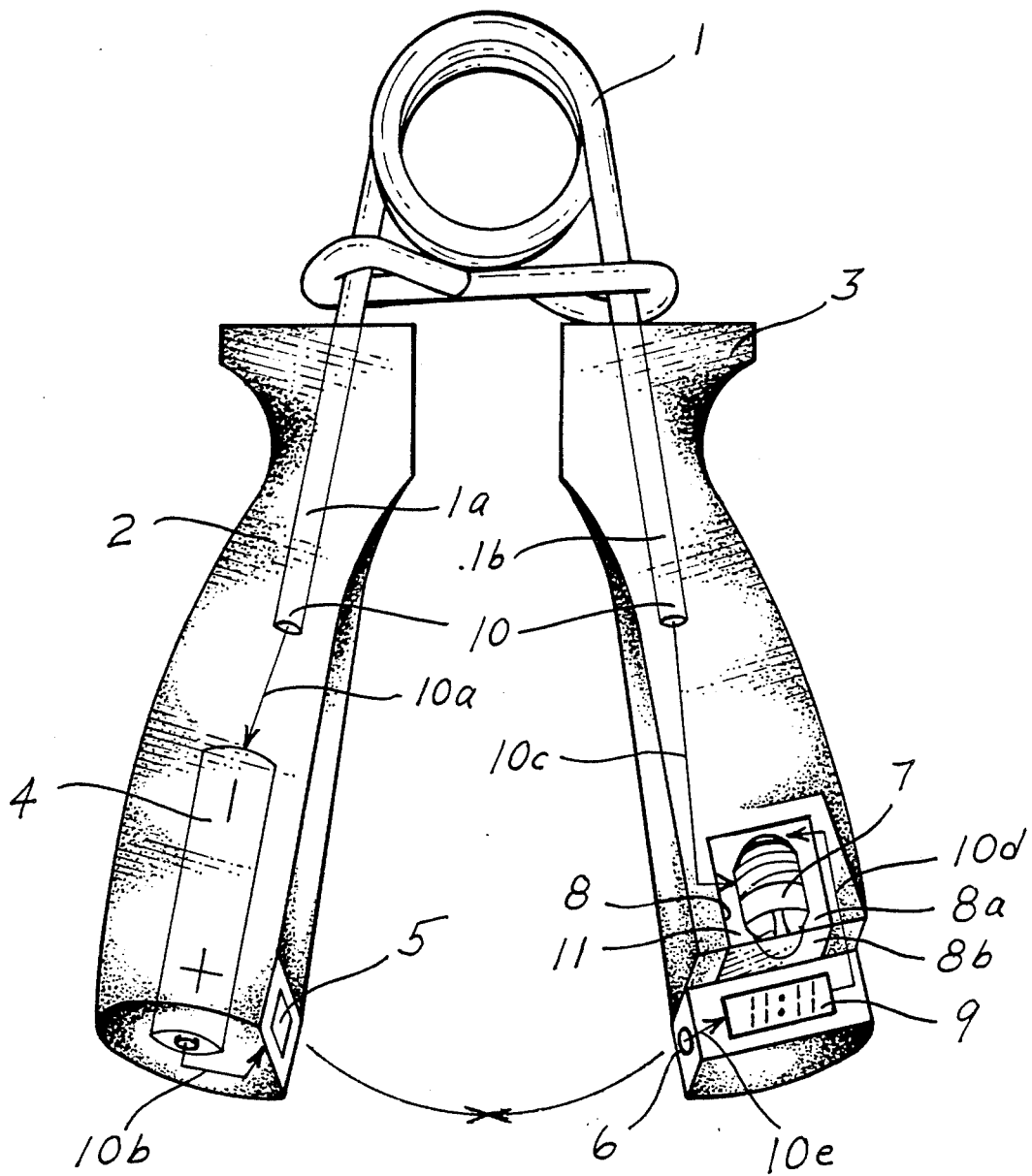

HANDGRIP, WITH LIGHT AND TIMER

FIELD OF THE INVENTION

The invention resides in the broad field of physical fitness, but particularly to a specific device for exercising the hand.

CROSS REFERENCE

My prior patent, No. 4,433,364, dated February 21, 1984.

OBJECTS OF THE INVENTION

The principal object of the invention is to provide a handgrip that indicates to the user the length of time that it is held in contracted, or fully squeezed, condition.

DESCRIPTION OF A PREFERRED EMBODIMENT

In the drawings,

The single figure is a perspective view of the handgrip made according to the present invention. Referring to the invention generally, the handgrip includes a pair of handles that are normally spread apart. It is held in the hand and the handles squeezed, moving them toward each other, against a spring means, the object being that in the squeezing of the handles, the muscles in the hand are developed, and in the course of so squeezing them, the closer they are squeezed together, the greater pressure is required and corresponding exercise of the muscles in the hand, the ultimate position being interengagement of the handles. The handgrip includes a light bulb that is lighted when the handles are so interengaged, to indicate that fact to the user. The handgrip of the present invention also includes a timer that is actuated in response to the handles being in interengagement, to indicate to the user the length of time that they are held in that interengagement.

Referring to the drawings in detail, the handles are indicated at 2, 3 and they are mounted on a coil spring 1 having terminal or end elements 1a, 1b embedded in the handles. The coil spring has a coil disposed longitudinally beyond the ends of the handles and it provides a pivot means for swinging of the handles toward and from each other. The coil spring with the terminal extensions is electrically conductive, constituting a portion of an electrical circuit utilized in the device, to be referred to again hereinbelow.

The handles 2, 3 may be made of any suitable material, such as plastic that may be molded. Electrical contacts 5, 6 are provided on the interfacing surfaces of the handles, at the ends of the handles remote from the coil spring 1, or the free and swinging ends thereof.

Embedded in one of the handles, such as 2, is a battery 4, and embedded in the other handle, 3, is a light bulb 7 and a timer 9.

The reference numeral 10 indicates a plurality of conductors, to be individually identified, in a circuit which incorporates the battery, the light bulb and the timer. A conductor 10a leads from the terminal 1a to the battery 4, and a conductor 10b leads from the battery to the contact 5.

In the other handle, 3, a conductor 10c leads from the terminal 1b to the base end of the light bulb 7, while another conductor 10d leads from the light bulb to the timer 9 at one end of the latter. From the other end of the timer another conductor 10e leads to the contact 6.

Broadly stated, when the handles are aqueezed together, the contacts 5, 6 interengage completing the circuit in the handgrip.

The numeral 8 indicates a cavity or recess which may be referred to as a window or opening, in the handle 3, in which the light bulb 7 is positioned. Preferably the window is provided with a cover or pane 11, which is transparent, and may be tinted or colored. The window has a front opening 8a and an end opening 8b, the front opening 8a being directed toward the user in the normal holding of the handgrip, i. e., on the front thereof. The end opening 8b, also covered by a portion of the pane 11, is directed longitudinally, and in position for enabling the light rays to fall directly on the timer 9, for illuminating the latter for easy observation by the user.

The timer 9 is of known kind, preferably of the kind that resets itself when the circuit is open or broken, and when it is energized, it advances, of course, to indicate the time. In the use of the device, when the user squeezes the handles, and contracts them to fully contracted position, and the contacts 5, 6 interengage, the light bulb 7 is illuminated, indicating to the user that the utmost position has been reached. This relieves him of the requirement for attention to determine whether the handles actually remain fully contracted position. At the same time the timer 9 is advanced and the user knows how long a period of time the handgrip is in fully squeezed position. This also relieves the user of constant attention for determining whether the handgrip is in fully squeezed position, by some other means, such as by watching a distant clock. It will be understood of course that the timer 9 may be of type that requires manual resetting, to enable the user to observe the actual period of time, even after he relaxes his grip.

Heretofore, one of the means for indicating whether the handles were in fully advanced or contracted position was to place a coin between the swinging ends of the handles, the coin dropping when the handles were released.

I claim:

1. A handgrip comprising,
a pair of elongated handles to be gripped by the hand, means mounting the handles together for movement of the handles toward and from each other in pivotal movement about a pivot axis that is disposed longitudinally beyond the handles whereby substantially the whole body of the handgrip is disposed longitudinally beyond the pivot axis,
the mounting means including spring means biasing the handles apart and yielding to enable the handles to be moved toward each other into interengagement, and the spring means being of great strength whreby the handles can be moved into such interengagement only by the full strength of the hand,
the handgrip including an electrical circuit which itself includes a battery, timer, light bulb, and contacts, and the contacts being exposed for non-yielding interengagmenet in response to the handles being moved into interengagement and effective when so interengaged for completing circuit and connecting the timer in circuit and thereby effecting operation of the timer, the electric circuit being normally open, and closed only when the handles are interengaged, the timer being inoperative when the circuit is open, the light bulb being lighted when the circuit is completed, and positioned for eady observation by the user in the normal use of the handgrip, the light bulb and timer being so relatively positioned that the light bulb when lighted illuminates the timer, the light bulb and timer being mounted in the same handle, at the swinging end of the handle, the timer being beyond the light bulb in the direction toward the end of the handle, and said handle having a front opening presenting the light bulb to the user in the normal holding of the handgrip, and an end opening effective for directing light rays longitudinally of the handle and onto the timer and illuminating the timer.

* * * * *